United States Patent
Yamagata et al.

(10) Patent No.: US 7,122,173 B2
(45) Date of Patent: Oct. 17, 2006

(54) AGENT FOR THE TREATMENT OF BLADDER IRRITATIVE SYMPTOMS ACCOMPANIED BY BENIGN PROSTATIC HYPERPLASIA

(75) Inventors: Tsuyoshi Yamagata, Sunto-gun (JP); Kaoru Atsuki, Chiyoda-ku (JP); Tetsuji Ohno, Sunto-gun (JP); Shiro Shirakura, Sunto-gun (JP); Akira Karasawa, Sunto-gun (JP); William C. de Groat, Pittsburgh, PA (US); Naoki Yoshimura, Pittsburgh, PA (US); Adrian Sculptoreanu, Pittsburgh, PA (US)

(73) Assignees: Kyowa Hakko Kogyo Co., Ltd., Tokyo (JP); University of Pittsburgh, PA (US)

( * ) Notice: Subject to any disclaimer, the term of this patent is extended or adjusted under 35 U.S.C. 154(b) by 400 days.

(21) Appl. No.: 10/473,348

(22) PCT Filed: Mar. 29, 2002

(86) PCT No.: PCT/US02/09575

§ 371 (c)(1),
(2), (4) Date: Sep. 30, 2003

(87) PCT Pub. No.: WO02/078633

PCT Pub. Date: Oct. 10, 2002

(65) Prior Publication Data

US 2004/0122078 A1    Jun. 24, 2004

Related U.S. Application Data

(60) Provisional application No. 60/279,699, filed on Mar. 30, 2001.

(51) Int. Cl.
*A61K 10/00* (2006.01)
*A61K 49/00* (2006.01)

(52) U.S. Cl. .......................... 424/9.8; 424/9.2
(58) Field of Classification Search ............... 424/9.2, 424/9.8
See application file for complete search history.

(56) References Cited

U.S. PATENT DOCUMENTS 5,510,386 A   4/1996   Empfield et al. ........... 514/603
6,211,227 B1   4/2001   Yoshida et al. ............. 514/431
2004/0132803 A1   7/2004   Yamagata et al. .......... 514/431

FOREIGN PATENT DOCUMENTS

EP    0 979 821    2/2000
WO    98/46587    10/1998

OTHER PUBLICATIONS

DeGroat, "A Neurologic Basis for the Overactive Bladder", *Urology*, vol. 50 (1997), pp. 36-52.
Robbins, "Clinical Applications of Capsaicinoids", *The Clinical Journal of Pain*, vol. 16, No. 2 (2000), pp. S86-S89.
Chai, et al., "The Incidence of a Positive Ice Water Test in Bladder Outlet Obstructed . . . ", *The Journal of Urology*, vol. 160, (1998), pp. 34-38.
Steers, et al., "Alterations in Afferent Pathways From the Urinary Bladder of the Rat in Response . . . ", *The Journal of Comparative Neurology*, vol. 310 (1991), pp. 401-410.
Gold, et al., "Characterization of Six Voltage-Gated $K^+$ Currents in Adult Rat Sensory Neurons", *Journal of Neurophysiology*, vol. 75, No. 6 (1996), pp. 2629-2646.
Yoshimura, et al., "Different types of $Na^+$ and A-type $K^+$ currents in dorsal root gangllon neurons . . . ", *Journal of Physiology*, vol. 494.1 (1996)), pp. 1-16.
Saito, et al., "Effects of Partial Outlet Obstruction of the rat Urinary Bladder on Micturition characteristics, DNA Synthesis . . . ", *Journal of Urology*, vol. 150 (1993), pp. 1045-1051.
Cruz, et al., "Desensitization of Bladder Sensory Fibers by Intraversical capsaicin Has Long Lasting Clinical and . . . ", *The Journal of Urology*, vol. 157 (1999), pp. 585-589.
Yoshimura, et al., "Increased Excitability of Afferent Neurons Innervating Rat Urinary . . . ", *The Journal of Neuroscience*, vol. 19, No. 11 (1999), pp. 4644-4653.
Cheng, et al., "Effect of capsaicin on micturition and associated reflexes in chronic spinal rats", *Brain Research*, vol. 678 (1995), pp. 40-48.
Malmgren, et al., "Effects of Pinacidil and Cromakalim (BRL 34915) on Bladder Function . . . ", *The Journal of Urology*, vol. 142 (1989), pp. 1134-1138.

*Primary Examiner*—Vickie Kim
(74) *Attorney, Agent, or Firm*—Fitzpatrick, Cella, Harper & Scinto

(57) ABSTRACT

The present invention provides an agent for the treatment of bladder irritative symptoms accompanied by benign prostatic hyperplasia, comprising, as an active ingredient, a compound having a slowly-inactivating A-type $K^+$ channel opening activity or a pharmaceutically acceptable salt thereof, and a method for screening agents for the treatment of bladder irritative symptoms accompanied by benign prostatic hyperplasia, comprising measuring a slowly-inactivating A-type $K^+$ channel opening activity as an index.

1 Claim, No Drawings

AGENT FOR THE TREATMENT OF BLADDER IRRITATIVE SYMPTOMS ACCOMPANIED BY BENIGN PROSTATIC HYPERPLASIA

This application is a 371 of PCT/US02/09575 filed Mar. 29, 2002 which claims benefit of Provisional Ser. No. 60/279,699 filed March 30, 2001.

FIELD OF THE INVENTION

The present invention relates to agents for the treatment of bladder irritative symptoms accompanied by benign prostatic hyperplasia.

BACKGROUND OF THE INVENTION

Benign prostatic hyperplasia (BPH) is a benign adenoma derived from a transitional region of the prostate which is present surrounding the urethra. Patients with BPH complain of bladder outlet obstructive symptoms or bladder irritative symptoms. Examples of the bladder outlet obstructive symptoms include the delayed initiation of micturition, abdominal muscle straining to void, reduced urinary flow rate, intermittency of urinary stream, post micturition dribble, prolonged voiding time, overflow incontinence, and the like. Examples of the bladder irritative symptoms include increased urinary frequency in the daytime or nighttime, urinary urgency, feeling of incomplete emptying, reduced voided volume during a single micturition, and the like. Functional obstruction and mechanical obstruction are involved in the development of these urinary disturbances due to BPH. These functional obstruction and mechanical obstruction further cause secondary changes in detrusor or nerves, and induce complex morbid states involving bladder irritative symptoms and bladder outlet obstructive symptoms.

As the therapeutic drug for BPH, for example, $\alpha_1$-adrenoceptor blockers, anti-androgen drugs, plant preparations, amino acid preparations or the like are used. Among these, examples of the $\alpha_1$-adrenoceptor blockers include tamusulosin hydrochloride, prazosin hydrochloride, terazosin hydrochloride, urapidil, and the like. As the anti-androgen drugs, chlormazinone acetate, allylestrenol, gestonorone caproate, oxendolone, finasteride or the like are used. The $\alpha_1$-adrenoceptor blockers inhibit functional obstruction of the urethra, by inhibiting the contraction of prostate smooth muscles induced by activation of $\alpha_1$-adrenoceptors with noradrenaline secreted from the sympathetic nerve. The anti-androgen drugs inhibit mechanical obstruction, by ameliorating the prostatic hyperplasia itself and thus reducing the urethra. However, the $\alpha_1$-adrenoceptor blockers and the anti-androgen drugs are effective only for the bladder outlet obstructive symptoms of BPH, but their effects for improving bladder irritative symptoms are usually insufficient. The plant preparations and amino acid preparations have an anti-inflammatory activity, an anti-edema activity, or the like and can improve the symptoms by alleviating the transitional disorder in the bladder neck; however, their effects are weak and the dose required is large so that they are a burden to the BPH patients that are usually old. Also, since there is a risk of causing increased residual urine and urinary retention for using anti-cholinergic agents, the use of anti-cholinergic agents is prohibited or restricted for the patients with BPH. Currently, there is no drug available that alleviates the bladder irritative symptoms associated with BPH.

Storage and voiding of urine are physiologically controlled by complex reflex pathways including peripheral and central nervous systems (*Urology*, 50 Suppl. 6A: 36–52 (1997)). Feeling of the filled bladder is transferred to the central nervous system via two bladder afferent neurons, the Aδ-fiber and the C-fiber. Under the normal condition, the C-fiber is not involved in the urine voiding (silent); however, the C-fiber is known to be activated and involved in the irritable bladder (*Clinical J. Pain*, 16, S86–89 (2000)). Moreover, about 70% of BPH patients show the positive reaction to the ice water test, indicating the activated sensory C-fiber, and the patients frequently show bladder irritative symptoms accompanied by the activation of C-fiber (*J. Urol.*, 160: 34–38 (1998)). Also, it has been shown that sprouting of sensory nerves occurs in the spinal cord of a rat in which urethra is partially obstructed, as is the case with BPH (*J. Comp. Neurol.*, 310: 401–410 (1991)). Since such sensory nerves showing sprouting exhibit capsaicin sensitivity, the nerves are the C-fiber, and thus activation of the C-fiber has been confirmed in rats with the bladder outlet obstruction. Collectively, there is accumulating evidence that the C-fiber is involved in the development of bladder irritative symptoms associated with BPH.

The potassium ($K^+$) channel is present on cell membranes of various tissues and shows various physiological activities via the control of membrane potential. The $K^+$ channel is classified into various types depending on the voltage-dependency, $Ca^{++}$-sensitivity, and other properties of the channel. The slowly-inactivating A-type $K^+$ channel is expressed in capsaicin-sensitive dorsal root ganglion (DRG) cells (*J. Neurophysiol.*, 75: 2629–2646 (1996)), and controls excitability of the C-fiber (*J. Physiol.*, 494: 1–16 (1996)).

DISCLOSURE OF THE INVENTION

According to the these observations, we have made the hypothesis that the bladder irritative symptoms associated with BPH can be alleviated by reducing excitability of the C-fiber through opening the slowly-inactivating A-type $K^+$ channel. We have found a compound having a slowly-inactivating A-type $K^+$ channel opening activity or a pharmaceutically acceptable salt thereof is useful for the treatment of bladder irritative symptoms accompanied by BPH, and we have achieved the present invention.

An object of the present invention is to provide an excellent agent for the treatment of bladder irritative symptoms accompanied by BPH.

The present invention relates to (1) an agent for the treatment of bladder irritative symptoms accompanied by BPH, comprising, as an active ingredient, a compound having a slowly-inactivating A-type $K^+$ channel opening activity or a pharmaceutically acceptable salt thereof, and (2) the agent for the treatment of bladder irritative symptoms accompanied by BPH according to (1), wherein the compound having a slowly-inactivating A-type $K^+$ channel opening activity is N-(5,5-dioxido-10-oxo-4,10-dihydrothieno[3,2-c][1]benzothiepin-9-yl)-3,3,3-trifluoro-2-hydroxy-2-methylpropanamide.

The present invention relates to (3) a method for the treatment of bladder irritative symptoms accompanied by BPH, which comprises administering a therapeutically effective amount of a compound having a slowly-inactivating A-type $K^+$ channel opening activity, or a pharmaceutically acceptable salt thereof, and (4) use of a compound having a slowly-inactivating A-type $K^+$ channel opening activity, or a pharmaceutically acceptable salt thereof for the manufacture of the agent for the treatment of bladder irritative symptoms accompanied by BPH.

Furthermore, the present invention relates to (5) a method for screening agents for the treatment of bladder irritative symptoms accompanied by BPH, comprising measuring a slowly-inactivating A-type K$^+$ channel opening activity as an index.

The term "compound having a slowly-inactivating A-type K$^+$ channel opening activity" as used herein means all compounds having a slowly-inactivating A-type K$^+$ channel opening activity regardless of a novel compound or a known compound and without limitation to the structure of compounds, so long as they have the slowly-inactivating A-type K$^+$ channel opening activity as one of their properties.

The compounds having a slowly-inactivating A-type K$^+$ channel opening activity used in the present invention include (S)-(+)-N-(5,5-dioxido-10-oxo-4,10-dihydrothieno[3,2-c][1]benzothiepin-9-yl)-3,3,3-trifluoro-2-hydroxy-2-methylpropanamide (Compound 1). Compound 1 is the same as Compound 1-25, described in WO 98/46587.

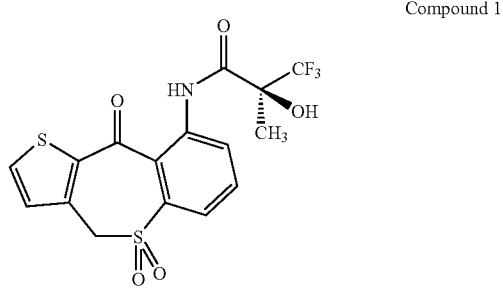

Compound 1

In the screening method of the present invention, the method for measuring a slowly-inactivating A-type K$^+$ channel opening activity is not particularly limited, but examples thereof include methods descried in Test Examples 1 and 2 described below.

The pharmacological activities of the compound used in the present invention are described below based on Test Examples.

TEST EXAMPLE 1

Facilitatory Effects on Slowly-Inactivating K$^+$ Currents in DRG Cells

Materials and Methods

Animal Preparation:

Experiments were performed on adult female Sprague Dawley rats. First and second series of the experiments were performed, respectively, in unidentified DRG neurons and a specific population of DRG neurons innervating the urinary bladder. The population of DRG neurons that innervate the urinary bladder were labeled by retrograde axonal transport of the fluorescent dye, Fast Blue (4% w/v) (Polyloy, Gross Umstadt, Germany), injected into the wall of the bladder in halothane-anesthetized animals 7 days before the dissociation. The dye was injected with a 28 gauge needle at three to six sites on the dorsal surface of the organ (5–6 µL per site, total volume of 20–30 µL). Each injection site was washed with saline to minimize contamination of adjacent organs with the dye.

Cell Dissociation:

Freshly dissociated neurons from DRG were prepared from halothane-anesthetized animals. L6 and S1 DRG were dissected from animals and then dissociated in a shaking bath for 25 minutes at 35° C. with 5 mL DMEM (Sigma) containing 0.3 mg/mL trypsin (Type 3, Sigma), 1 mg/mL collagenase (Type 1, Sigma), and 0.1 mg/mL deoxyribonuclease (Type 4, Sigma). Trypsin inhibitor (Type 2a, Sigma) was then added thereto to neutralize the activity of trypsin. Individual DRG cell bodies were isolated by trituration and then plated on a poly-L-lysine-coated 35 mm Petri dishes.

Electrical Recordings:

Dye-labeled primary afferent neurons that innervate the urinary bladder were identified using an inverted phase-contrast microscope (Nikon, Tokyo, Japan) with fluorescent attachments (UV-1A filter; excitation wavelength, 365 nm). Gigaohm-seal whole-cell recordings were performed at room temperature (20–22° C.) on each labeled neuron in a culture dish that usually contained three to seven labeled cells among a few hundred unlabeled neurons. The internal solution contained (in mmol/L): KCl 140, CaCl$_2$ 1, MgCl$_2$ 2, EGTA 11, HEPES 10, Mg-ATP 2, and Tris-GTP 0.4 adjusted to pH 7.4 with KOH. Patch electrodes had resistances of 1–4 M Ω when filled with the internal solution. Neurons were superfused at a flow rate of 1.5 mL/minutes with an external solution containing (in mmol/L): NaCl 150, KCl 5, CaCl$_2$ 2.5, MgCl$_2$ 1, HEPES 10, and D-glucose 10, adjusted to pH 7.4 with NaOH. All recordings were made with an Axopatch-1D patch-clamp amplifier (Axon Instruments, Foster City, Calif.), and data were acquired and analyzed by PCLAMP software (Axon Instruments).

In voltage-clamp recordings, outward K$^+$ currents and inward Na$^+$ currents were measured. For the isolation of K$^+$ currents, the external solution was changed to one containing (in mmol/L): choline-Cl 150, KOH 5, CaCl$_2$ 0.03, HEPES 10, Mg(OH)$_2$ 3, and D-glucose 10, adjusted to pH 7.4 with HCl.

In first series of experiments using unidentified DRG neurons, outward K$^+$ currents were evoked by voltage steps to +60 mV, 800 ms long from a holding potentials of −90 mV, this was followed by a 1-second conditioning pre-pulse to −20 mV followed by a second pulse to +60 mV, identical to the first in the sequence. In the second series of experiments using Fast Blue-labeled bladder afferent neurons, slowly-inactivating A-type K$^+$ currents were isolated by subtraction of outward K$^+$ currents activated from a holding potential of −40 mV (on the condition of inactivation of the majority of slowly-inactivating A-type K$^+$ currents) from those activated from a holding potential of −120 mV (on the condition of full activation of slowly-inactivating A-type K$^+$ currents). A compound was added cumulatively, starting with a lower concentration. Currents were measured at the maximum (peak) and normalized to control (before addition of the compound).

Inward Na$^+$ currents were evoked by voltage steps to +60 mV, 800 ms long from a holding potentials of −90 mV. Currents were measured at the maximum (peak) and normalized to control (before addition of the compound).

The results obtained in unidentified DRG neurons are shown in Tables 1 to 5, and the results obtained in capsaicin-sensitive bladder afferent neurons are shown in Table 6. Table 1 shows the activity of Compound 1 upon changes in currents when the holding potential is −90 mV (on the condition of activation of slowly-inactivating A-type K$^+$ currents) or −20 mV (on the condition of inactivation of slowly-inactivating A-type K$^+$ currents). Table 2 shows the activity of Compound 1 in the presence of 20 mmol/L tetraethylammonium, Table 3 shows the activity of Compound 1 in the presence of 5 μmol/L verapamil, and Table 4 shows the activity of Compound 1 in the presence of 60 mmol/L tetraethylammonium. Table 5 shows the activity of Compound 1 upon $Na^+$ currents. In Tables 1 to 5, n means the number of cases.

TABLE 1

| Compound 1 (mol/L) | HP: −90 mV | n | HP: −20 mV | n |
|---|---|---|---|---|
| $5.0 \times 10^{-9}$ | 1.01 ± 0.03 | 7 | 0.98 ± 0.02 | 7 |
| $1.0 \times 10^{-8}$ | 0.99 ± 0.08 | 3 | 0.98 ± 0.04 | 3 |
| $2.5 \times 10^{-8}$ | 1.07 ± 0.03 | 5 | 1.01 ± 0.03 | 5 |
| $5.0 \times 10^{-8}$ | 1.07 ± 0.02 | 16 | 1.00 ± 0.01 | 16 |
| $1.0 \times 10^{-7}$ | 1.12 ± 0.03 | 10 | 1.02 ± 0.01 | 10 |
| $5.0 \times 10^{-7}$ | 1.15 ± 0.03 | 7 | 1.01 ± 0.02 | 7 |
| $1.0 \times 10^{-6}$ | 1.06 ± 0.02 | 13 | 1.00 ± 0.02 | 13 |
| $1.0 \times 10^{-5}$ | 0.96 ± 0.05 | 8 | 0.88 ± 0.07 | 8 |
| $5.0 \times 10^{-5}$ | 0.83 ± 0.09 | 3 | 0.81 ± 0.08 | 3 |

Table 1 shows the activity of Compound 1 on currents measured by a voltage clamp using unidentified DRG cells. The currents at a holding potential (HP) of −90 mV are results of the measurement of slowly-inactivating A-type $K^+$ currents, and the currents at an HP value of −20 mV are results of the measurement of delayed rectifier $K^+$ currents. Table 1 shows that Compound 1 increases slowly-inactivating A-type $K^+$ currents with a peak compound concentration of from $1\times10^{-7}$ to $5\times10^{-7}$ mol/L, but does not have no influences (little influences) upon delayed rectifier $K^+$ currents. Also, effects (values) of Compound 1 are shown by relative values when the values before the drug application is defined as 1.

TABLE 2

| Compound 1 (mol/L) | HP: −90 mV | n | HP: −20 mV | n |
|---|---|---|---|---|
| $5.0 \times 10^{-9}$ | 1.02 ± 0.02 | 8 | 0.99 ± 0.00 | 8 |
| $5.0 \times 10^{-8}$ | 1.08 ± 0.02 | 10 | 0.99 ± 0.01 | 10 |
| $1.0 \times 10^{-7}$ | 1.10 ± 0.01 | 3 | 0.99 ± 0.02 | 3 |
| $5.0 \times 10^{-7}$ | 1.15 ± 0.04 | 14 | 1.01 ± 0.01 | 14 |
| $1.0 \times 10^{-6}$ | 1.19 ± 0.05 | 4 | 1.00 ± 0.00 | 4 |
| $5.0 \times 10^{-6}$ | 1.16 ± 0.03 | 10 | 0.98 ± 0.01 | 10 |
| $1.0 \times 10^{-5}$ | 1.19 ± 0.01 | 3 | 1.01 ± 0.02 | 3 |
| $5.0 \times 10^{-5}$ | 0.91 ± 0.04 | 8 | 0.84 ± 0.06 | 8 |
| $5.0 \times 10^{-4}$ | 0.29 ± 0.02 | 4 | 0.25 ± 0.04 | 4 |

Table 2 shows the activity of Compound 1 in the presence of tetraethylammonium as a blocker of delayed rectifier $K^+$ currents. Since Compound 1 shows the same results in the presence of the blocker of delayed rectifier $K^+$ currents, it is suggested that the $K^+$ currents increasing effect of Compound 1 is not mediated by the delayed rectifier $K^+$ channel.

TABLE 3

| Compound 1 (mol/L) | HP: −90 mV | n | HP: −20 mV | n |
|---|---|---|---|---|
| $5.0 \times 10^{-8}$ | 1.03 ± 0.02 | 3 | 1.00 ± 0.00 | 3 |
| $1.0 \times 10^{-7}$ | 1.13 ± 0.02 | 4 | 1.00 ± 0.01 | 4 |
| $5.0 \times 10^{-7}$ | 1.17 ± 0.03 | 8 | 1.00 ± 0.01 | 8 |
| $1.0 \times 10^{-6}$ | 1.11 ± 0.03 | 5 | 1.00 ± 0.01 | 5 |
| $5.0 \times 10^{-6}$ | 1.02 ± 0.03 | 6 | 1.01 ± 0.01 | 6 |
| $1.0 \times 10^{-5}$ | 0.99 ± 0.02 | 6 | 1.00 ± 0.02 | 6 |
| $5.0 \times 10^{-5}$ | 0.94 ± 0.02 | 9 | 0.98 ± 0.01 | 9 |
| $5.0 \times 10^{-4}$ | 0.61 ± 0.05 | 6 | 0.83 ± 0.06 | 6 |

Table 3 shows the activity of Compound 1 in the presence of verapamil as a blocker of delayed rectifier $K^+$ currents. Since the results obtained in Table 3 are similar to those in Table 2, it is suggested that the $K^+$ currents increasing effect of Compound 1 is not mediated by the delayed rectifier $K^+$ channel.

TABLE 4

| Compound 1 (mol/L) | HP: −90 mV | n | HP: −20 mV | n |
|---|---|---|---|---|
| $5.0 \times 10^{-8}$ | 1.08 ± 0.02 | 12 | 1.00 ± 0.01 | 12 |
| $5.0 \times 10^{-7}$ | 1.11 ± 0.03 | 12 | 0.97 ± 0.03 | 12 |
| $5.0 \times 10^{-6}$ | 1.14 ± 0.05 | 10 | 0.97 ± 0.02 | 10 |
| $5.0 \times 10^{-5}$ | 1.15 ± 0.08 | 7 | 0.95 ± 0.03 | 7 |
| $5.0 \times 10^{-4}$ | 0.56 ± 0.05 | 5 | 0.54 ± 0.02 | 5 |

Table 4 shows the activity of Compound 1 in the presence of high concentration tetraethylammonium (TEA). The high concentration tetraethylammonium (TEA) acts as a blocker of delayed rectifier $K^+$ currents. Since the results obtained in Table 4 are also similar to those in Table 2, it is suggested that the $K^+$ currents increasing effect of Compound 1 is not mediated by the delayed rectifier $K^+$ channel.

TABLE 5

| Compound 1 (mol/L) | $Na^+$ ion currents | n |
|---|---|---|
| $5.0 \times 10^{-8}$ | 0.99 ± 0.01 | 9 |
| $5.0 \times 10^{-7}$ | 0.99 ± 0.01 | 9 |
| $1.0 \times 10^{-6}$ | 0.99 ± 0.02 | 4 |
| $5.0 \times 10^{-6}$ | 1.00 ± 0.00 | 6 |
| $5.0 \times 10^{-5}$ | 1.00 ± 0.01 | 6 |
| $5.0 \times 10^{-4}$ | 1.00 ± 0.01 | 5 |

Table 5 shows the activity of Compound 1 upon $Na^+$ currents in DRG cells. It is evident from Table 5 that Compound 1 does not exert influence upon $Na^+$ currents.

TABLE 6

| Compound 1 (mol/L) | A-type $I_K$ (HP: −120 mV) − (HP: −40 mV) | n | Delayed rectifier HP: −40 mV | n |
|---|---|---|---|---|
| $1.0 \times 10^{-6}$ | 1.26 ± 0.03 | 6 | 1.10 ± 0.01 | 6 |

Table 6 shows the activity of Compound 1 upon slowly-inactivating A-type $K^+$ currents ($I_K$) and delayed rectifier $K^+$ currents in Fast Blue-labeled bladder afferent neurons which were sensitive to capsaicin (presumed C-fiber neurons). Slowly-inactivating A-type $K^+$ currents were isolated by subtraction of outward $K^+$ currents activated from a holding potential of −40 mV (on the condition of inactivation of the majority of slowly-inactivating A-type $K^+$ currents) from those activated from a holding potential of −120 mV (on the condition of full activation of slowly-inactivating A-type $K^+$ currents). As demonstrated in unidentified DRG neurons, Table 6 shows that Compound 1 increases slowly-inactivating A-type $K^+$ currents, but have smaller influences upon delayed rectifier $K^+$ currents.

TEST EXAMPLE 2

Changes in Membrane Potential in DRG Cells

Material and Methods

Animal Preparation:

Experiments were performed on adult female Sprague Dawley rats. A population of unidentified DRG cells and a population of DRG neurons that innervate the urinary bladder were labeled by retrograde axonal transport of the fluorescent dye, Fast Blue (4% w/v) (Polyloy, Gross Umstadt, Germany) injected into the wall of the bladder in halothane-anesthetized animals 7 days before the dissociation. The dye was injected with a 28 gauge needle at three to six sites on the dorsal surface of the organ (5–6 μL per site, total volume of 20–30 μL). Each injection site was washed with saline to minimize contamination of adjacent organs with the dye.

Cell Dissociation:

Freshly dissociated neurons from DRG were prepared from halothane-anesthetized animals. L6 and S1 DRG were dissected from animals and then dissociated in a shaking bath for 25 minutes at 35° C. with 5 mL DMEM (Sigma) containing 0.3 mg/mL trypsin (Type 3, Sigma), 1 mg/mL collagenase (Type 1, Sigma), and 0.1 mg/ML deoxyribonuclease (Type 4, Sigma). Trypsin inhibitor (Type 2a, Sigma) was then added thereto to neutralize the activity of trypsin. Individual DRG cell bodies were isolated by trituration and then plated on a poly-L-lysine-coated 35 mm Petri dishes.

Electrical Recordings:

Dye-labeled primary afferent neurons that innervate the urinary bladder were identified using an inverted phase-contrast microscope (Nikon, Tokyo, Japan) with fluorescent attachments (UV-1A filter; excitation wavelength, 365 nm). Gigaohm-seal whole-cell recordings were performed within 6–8 hours after cell dissociation at room temperature (20–22° C.) on each labeled neuron in a culture dish that usually contained three to seven labeled cells among a few hundred unlabeled neurons. The internal solution contained (in mmol/L): KCl 140, $CaCl_2$ 1, $MgCl_2$ 2, EGTA 11, HEPES 10, Mg-ATP 2, and Tris-GTP 0.4 adjusted to pH 7.4 with KOH. Patch electrodes had resistances of 1–4 M Ω when filled with the internal solution. Neurons were superfused at a flow rate of 1.5 mL/minutes with an external solution containing (in mmol/L): NaCl 150, KCl 5, $CaCl_2$ 2.5, $MgCl_2$ 1, HEPES 10, and D-glucose 10, adjusted to pH 7.4 with NaOH. All recordings were made with an Axopatch-1D patch-clamp amplifier (Axon Instruments, Foster City, Calif.), and data were acquired and analyzed by PCLAMP software (Axon Instruments).

In current-clamp recordings, membrane potential of DRG cell were measured before and after compound applications. The membrane potentials were normalized to control (before addition of the compound).

Effect of Compound 1 on membrane potential is shown in Table 7.

TABLE 7

| Compound 1 (mol/L) | Membrane potential (mV) | n |
|---|---|---|
| 0 | −47.95 ± 0.22 | 20 |
| $1.0 \times 10^{-9}$ | −48.10 ± 0.48 | 10 |
| $1.0 \times 10^{-8}$ | −49.80 ± 0.65 | 5 |
| $1.0 \times 10^{-7}$ | −57.17 ± 0.53 | 6 |
| $1.0 \times 10^{-6}$ | −53.67 ± 0.74 | 6 |
| $5.0 \times 10^{-6}$ | −50.50 ± 0.88 | 4 |
| $5.0 \times 10^{-5}$ | −48.50 ± 1.28 | 4 |
| $5.0 \times 10^{-4}$ | −42.67 ± 1.46 | 3 |

Table 7 shows the activity of Compound 1 upon membrane potential in DRG cells. It showed that Compound 1 increases slowly-inactivating A-type $K^+$ currents, namely increases outward currents to effect hyperpolarization (a negative change of membrane potential). This activity suggests reduction of excitability of DRG cells.

Based on the results of Test Examples 1 and 2, it was revealed that Compound 1 has an activity of increasing slowly-inactivating A-type $K^+$ currents.

TEST EXAMPLE 3

Activity of Inhibiting the Increased Urinary Frequency Accompanied by Partial Bladder Outlet Obstruction The test was carried out in accordance with the method of Saito et al. (*J. Urol.*, 150: 1045–1051 (1993)).

Male SD rats of 8 to 9 weeks of age (supplied by Japan SLC) were used in the test. Five to seven animals of these rats were put in each metal cage and reared by allowing them to freely take commercially available chow and water, in a rearing room at a room temperature of from 19 to 25° C. and a humidity of from 30 to 70% under illumination for 12 hours (from 7 a.m. to 7 p.m.) per day.

Partial urethra obstruction was induced in rats as a model of outlet obstruction mimicking BPH. Each rat was anesthetized by intraperitoneal administration of 50 mg/kg of pentobarbital sodium (Dainippon Pharmaceutical) and placed in dorsal position. The abdomen was cut in a length of about 1 cm by midline incision to expose the bladder, prostate and the urethra. The bladder neck and bladder base were peeled from the prostate, and two surgical sutures (No. 3, Natsume Seisakusho) were passed behind the urethra base. A polyethylene tube (PE-200; Becton Dickinson) was placed along the urethra, and the urethra was mildly double-ligated together with the tube. The ligation was carried out in such a manner that the urethra was not pressed by the polyethylene tube and the sutures were not loosened. The polyethylene tube was pulled out and the urethra was partially obstructed. The incised part of the abdomen was sutured with the surgical suture.

Five to seven days after the partial urethra constriction operation, the rats subjected to partial urethra obstruction and those subjected to sham-operation were put in metabolism cages (KN-649, Natsume Seisakusho). For acclimatization, rats were reared for 1 day with free drinking and feeding, and the urination test was started on the next day. Using an electronic force balance (HF-200; A and D), the amount of urination by rats was continuously measured as weight, and -recorded on a thermal array recorder (RTA-1200; Nihon Kohden) via a direct current amplifier (AD-641G; Nihon Kohden). The light period (9 to 18 o'clock) under illumination and the dark period (19 to 4 o'clock) under lights off were used as the data collecting periods, and the number of micturition and the urinary volume during these periods were measured to calculate urinary frequency (frequency of micturition per 9 hours), voided volume per micturition and total urine volume as the measuring parameters. In this case, the voided volume per micturition was calculated by dividing the total urine volume per 9 hours by the urinary frequency per 9 hours. Compound 1 or a solvent (0.5 w/v % aqueous methyl cellulose 400 cP (average viscosity: 400 centipoises) solution) was administered twice on the next day between 8 to 9 o'clock and 18 to 19 o'clock, and the number of micturition and urine volume during 9 to 18 o'clock and 19 to 4 o'clock were measured to obtain measured values similarly to the case of the previous day. In the sham-operation group, the urinary frequency, voided volume per micturition and the total urine volume on the first day of the urination test were compared with those in the urethra obstruction group. The urinary frequency, voided volume per micturition and the total urine volume in each group were calculated as average ±standard error.

The results of the urinary frequency, voided volume per micturition and the total urine volume are shown in Table 8, Table 9 and Table 10, respectively.

TABLE 8

| | Urinary frequency (micturitions/9 h) | |
|---|---|---|
| | Before administration | After administration |
| Light period (inactive period) | | |
| sham-operation group | 4.3 ± 0.6 | 5.2 ± 0.7 |
| Control group | 8.9 ± 1.0 | 9.0 ± 0.7 |
| Compound 1 | 8.7 ± 0.8 | 5.3 ± 0.4*** |
| Dark period (active period) | | |
| Sham-operation group | 7.3 ± 0.8 | 7.2 ± 1.1 |
| Control group | 8.6 ± 0.6 | 10.3 ± 1.0 |
| Compound 1 | 10.0 ± 1.3 | 6.7 ± 1.2* |

*$p < 0.05$
***$p < 0.001$ (comparison with the control group) (n = 6–7, Student's t-test)

TABLE 9

| | Voided volume per micturition (mL) | |
|---|---|---|
| | Before administration | After administration |
| Light period (inactive period) | | |
| Sham-operation group | 1.058 ± 0.154 | 0.947 ± 0.149 |
| Control group | 0.678 ± 0.102 | 0.584 ± 0.090 |
| Compound 1 | 0.577 ± 0.064 | 0.899 ± 0.127 |
| Dark period (active period) | | |
| Sham-operation group | 0.507 ± 0.093 | 0.630 ± 0.086 |
| Control group | 0.493 ± 0.047 | 0.475 ± 0.059 |
| Compound 1 | 0.362 ± 0.038 | 0.771 ± 0.160 |

TABLE 10

| | Total urine volume (mL/9 h) | |
|---|---|---|
| | Before administration | After administration |
| Light period (inactive period) | | |
| Sham-operation group | 4.29 ± 0.47 | 4.47 ± 0.50 |
| Control group | 5.68 ± 0.87 | 5.19 ± 0.86 |
| Compound 1 | 4.80 ± 0.31 | 4.76 ± 0.78 |
| Dark period (active period) | | |
| Sham-operation group | 3.48 ± 0.47 | 4.27 ± 0.74 |
| Control group | 4.29 ± 0.64 | 4.89 ± 0.69 |
| Compound 1 | 3.57 ± 0.57 | 4.83 ± 0.83 |

The results in Test Example 3 show that Compound 1 significantly reduced urinary frequency and tended to increase voided volume per micturition. Thus, it is considered that Compound 1 is useful for the treatment of increased urinary frequency accompanied by BPH.

TEST EXAMPLE 4

Activity of Increasing Bladder Capacity in Rats with Partial Outlet Obstruction

The test was carried out in accordance with the method of Saito et al. (*J. Urol.*, 150: 1145–1151 (1993)).

Male SD rats of 8 to 9 weeks of age (supplied by Japan SLC) were used in the test. Five to seven animals of these rats were put in each metal cage and reared by allowing them to freely take commercially available chow and water, in a rearing room at a room temperature of from 19 to 25° C. and a humidity of from 30 to 70% under illumination for 12 hours (from 7 a.m. to 7 p.m.) per day.

Partial urethra obstruction was induced in rats, as a model of urethral obstruction mimicking BPH. Each rat was anesthetized by intraperitoneal administration of 50 mg/kg of pentobarbital sodium (Dainippon Pharmaceutical) and placed in dorsal position. The abdomen was cut in a length of about 1 cm by median incision to expose the bladder, prostate and the urethra. The bladder neck and bladder base were peeled from the prostate, and two surgical sutures (No. 3, Natsume Seisakusho) were passed behind the urethra base. A polyethylene tube (PE-200; Becton Dickinson) was placed along the urethra, and the urethra was mildly double-ligated together with the tube. The ligation was carried out in such a manner that the urethra was not pressed by the polyethylene tube and the sutures were not loosened. The polyethylene tube was pulled out and the urethra was constricted.

On the same day of the above surgery, bladder catheter indwelling operation was carried out. The bladder was exposed, and a polyethylene tube (PE-50; Becton Dickinson) was inserted from the bladder top and fixed with a surgical suture. The other end was exposed subcutaneously from the back neck, plugged and then fixed to the skin with the surgical suture. The bladder was returned to the original position and the abdomen was sutured with the surgical suture.

Five to seven days after the urethra obstruction and catheter indwelling operations, the rats with partial urethra obstruction and those subjected to sham-operation were put in Ballman cages (KN-326-1, Natsume Seisakusho) under the restricted state, and a three-way cock was connected to the bladder catheter. A pressure transducer (DX-360; Nihon Kohden) was connected to one end of the three-way cock, and the intravesical pressure signal was amplified via a strain pressure amplifier (AP-601G; Nihon Kohden), measured by a polygraph (RPM-6008; Nihon Kohden) and recorded on a thermal array recorder (RTA-1200; Nihon Kohden). A syringe filled with physiological saline (Otsuka Pharmaceutical Industries, Tokushima, Japan) was connected to the other end of the three-way cock and fixed to an infusion pump (KDS 220; Neuroscience). An FD pickup (TB-611T; Nihon Kohden) equipped with a cup was placed on the downside of the Ballman cage and connected to the strain gauge pressure amplifier, and the micturition volume was recorded on the thermal array recorder as the tension change. After the completion of the preparation, physiological saline kept at room temperature was continuously injected into the bladder at a flow rate of 6 mL/h for about 30 minutes, and the animals periodically expressing micturition contraction were used in the test. After they are allowed to stand for 30 to 60 minutes, residual urine was manually expressed by finger pressure. Five minutes thereafter, the injection of physiological saline into the bladder was started again, and the injection was immediately stopped when micturition was observed. The bladder capacity was calculated from the period of time until expression of micturition (injection rate 6 mL/h×injection period). The residual urine volume was calculated by subtracting the micturition volume at the time of bladder contraction (voided volume per micturition) from the bladder capacity. By repeating 30 minutes of bladder injection of physiological saline 2 to 3 times, respective values were measured and used as the test compound or solvent pre-administration values. Then, the test compound or solvent (0.5 w/v % aqueous methyl cellulose 400 cP (average viscosity: 400 centipoises) solution) was orally administered. One, two and three hours after the administration, the bladder injection of physiological saline was carried out to measure the bladder capacity, micturition volume and the residual urine volume. The bladder capacity, micturition volume and the residual urine volume in each group were calculated as average±standard error.

The results of the bladder capacity, micturition volume and the residual urine volume are shown in Table 11, Table 12 and Table 13, respectively.

TABLE 11

| | Bladder capacity (mL) | | | |
|---|---|---|---|---|
| | before administration | 1 h after administration | 2 h after administration | 3 h after administration |
| Control | 0.42 ± 0.09 | 0.33 ± 0.09 | 0.28 ± 0.06 | 0.25 ± 0.06 |
| Compound 1 | 0.40 ± 0.04 | 0.54 ± 0.08 | 0.46 ± 0.07 | 0.44 ± 0.07 |

TABLE 12

| | micturition volume (mL) | | | |
|---|---|---|---|---|
| | before administration | 1 h after administration | 2 h after administration | 3 h after administration |
| Control | 0.29 ± 0.09 | 0.19 ± 0.08 | 0.15 ± 0.04 | 0.14 ± 0.03 |
| Compound 1 | 0.25 ± 0.04 | 0.36 ± 0.07 | 0.36 ± 0.07* | 0.27 ± 0.01** |

*$p < 0.05$,
**$p < 0.01$ (comparison with the control group)
(n = 6–7, Student's t-test)

TABLE 13

| | Residual urine volume (mL) | | | |
|---|---|---|---|---|
| | before administration | 1 h after administration | 2 h after administration | 3 h after administration |
| Control | 0.13 ± 0.05 | 0.14 ± 0.05 | 0.13 ± 0.03 | 0.11 ± 0.05 |
| Compound 1 | 0.15 ± 0.02 | 0.18 ± 0.07 | 0.10 ± 0.05 | 0.18 ± 0.07 |

According to Test Example 4, Compound 1 tended to increase bladder capacity and significantly increased micturition volume. Thus, it is considered that Compound 1 has an ability of ameliorating storage disturbances accompanied by partial urethra obstruction caused by BPH.

Test Examples 3 and 4 show that Compound 1 has an ability of remitting bladder irritative symptoms accompanied by BPH, indicating that the compound having a slowly-inactivating A-type $K^+$ channel opening activity or a pharmaceutically acceptable salt thereof is useful as an agent for the treatment of bladder irritative symptoms accompanied by BPH.

TEST EXAMPLE 5

Acute Toxicity Test

The test compound was administered orally or intraperitoneally to 3 animals per group of dd male mice (body weight, 20±1 g). Minimum lethal dose (MLD) value was obtained by observing mortality on the 7th day after the administration.

As a result, MLD of Compound 1 was >1,000 mg/kg by oral administration.

Based on the results of Test Examples 1 to 5, the compound having a slowly-inactivating A-type $K^+$ channel opening activity or a pharmaceutically acceptable salt thereof is useful as an agent for the treatment of bladder irritative symptoms accompanied by BPH.

The compound having a slowly-inactivating A-type $K^+$ channel opening activity or a pharmaceutically acceptable salt thereof can be used as it is or in various dose forms. Pharmaceutical compositions of the present invention can be produced by uniformly mixing an effective amount of the compound having a slowly-inactivating A-type $K^+$ channel opening activity or a pharmaceutically acceptable salt thereof as an active ingredient with a pharmacologically acceptable carrier. It is preferred that these pharmaceutical compositions are in a unit dose form suitable for oral or parenteral (including intravenous) administration or the like.

In preparing a composition in the oral dose form, certain useful pharmacologically acceptable carriers can be used. For example, oral liquid preparations such as suspensions or syrups can be produced using water; saccharides, such as sucrose, sorbitol, fructose, or the like; glycols, such as polyethylene glycol, propylene glycol, or the like; oils, such as sesame oil, olive oil, soybean oil, or the like; antiseptics, such as p-hydroxybenzoic acid esters or the like; flavors, such as strawberry flavor, peppermint, or the like; or the like. Capsules, tablets, powders and granules can be produced using fillers, such as lactose, glucose, sucrose, mannitol, or the like; disintegrators, such as starch, sodium alginate, or the like; lubricants, such as magnesium stearate, talc, or the like; binders, such as polyvinyl alcohol, hydroxypropylcellulose, gelatin, or the like; surfactants, such as fatty acid esters or the like; plasticizers, such as glycerine or the like; or the like. Tablets and capsules are the most useful unit oral administration preparations because of their easy administration. In producing tablets or capsules, solid pharmaceutical carriers are used.

In addition, injections can be prepared using a carrier comprising distilled water, a salt solution, a glucose solution or a mixture of salt water and a glucose solution. In this case, they are prepared as solutions, suspensions or dispersions using suitable auxiliaries in the conventional way.

The compound having a slowly-inactivating A-type $K^+$ channel opening activity or a pharmaceutically acceptable salt thereof can be administered orally in the above dose forms or parenterally as injections, and, although its effective dose and administration frequency may vary depending, for example, on the dose form, the age and body weight of each patient, and symptoms of the disease, from 1 to 900 mg/60 kg/day, preferably from 1 to 200 mg/60 kg/day, is suitable.

The embodiments of the present invention are described below based on Examples.

BEST MODE FOR CARRYING OUT THE INVENTION

EXAMPLE 1

Tablets

Tablets having the following composition were prepared in the conventional way.

Compound 1 (250 g) was mixed with 1598.5 g of mannitol, 100 g of sodium starch glycollate, 10 g of light anhydrous silicic acid, 40 g of magnesium stearate and 1.5 of yellow ferric oxide in the conventional way. The resulting mixture was applied to a tablet making machine having a punch and die of 8 mm in diameter (Purepress Correct-12, manufactured by Kikusui) to obtain tablets (containing 25 mg of the active component per one tablet).

The prescription is shown in Table 14.

TABLE 14

| Prescription | Compound 1 | 25 mg |
|---|---|---|
| | Mannitol | 159.85 mg |
| | Sodium starch glycollate | 10 mg |
| | Light anhydrous silicic acid | 1 mg |
| | Magnesium stearate | 4 mg |
| | Yellow ferric oxide | 0.15 mg |
| | | 200 mg |

EXAMPLE 2

Capsules

Capsules having the following composition were prepared in the conventional way.

Compound 1 (500 g) was mixed with 300 g of lactose, 100 g of light anhydrous silicic acid and 100 g of sodium lauryl sulfate in the conventional way. The resulting mixture was packed in hard capsules No. 1 (100 mg per one capsule) using an encapsulation machine (LZ-64, manufactured by Zanasi) to obtain capsules (containing 50 mg of the active component per one capsule).

The prescription is shown in Table 15.

TABLE 15

| Prescription | Compound 1 | 50 mg |
|---|---|---|
| | Lactose | 30 mg |

TABLE 15-continued

| | Light anhydrous silicic acid | 10 mg |
|---|---|---|
| | Sodium lauryl sulfate | 10 mg |
| | | 100 mg |

EXAMPLE 3

Injections

Injections having the following composition are prepared in the conventional way.

Compound 1 (1 g) is dissolved in 100 g of purified soybean oil and 12 g of purified yolk lecithin and 25 g of glycerol for injection are added thereto. The resulting mixture is kneaded with distilled water for injection (total: 1,000 mL) and emulsified therein in the conventional way. The obtained dispersion is aseptically filtered using a 0.2 μm disposable membrane filter and then aseptically dispensed into glass vials in 2 ml portions to obtain injections (containing 2 mg of the active component per one vial).

The prescription is shown in Table 16.

TABLE 16

| Prescription | Compound 1 | 2 mg |
|---|---|---|
| | Purified soybean oil | 200 mg |
| | Purified yolk lecithin | 24 mg |
| | Glycerol for injection | 50 mg |
| | Distilled water for injection | 1.72 ml |
| | | 2.00 ml |

INDUSTRIAL APPLICABILITY

The present invention provides an agent for the treatment of bladder irritative symptoms accompanied by BPH, comprising, as an active ingredient, a compound having a slowly-inactivating A-type $K^+$ channel opening activity or a pharmaceutically acceptable salt thereof, and a method for screening agents for the treatment of bladder irritative symptoms accompanied by BPH, comprising measuring a slowly-inactivating A-type $K^+$ channel opening activity as an index.

The invention claimed is:

1. A method for screening agents for the treatment of bladder irritative symptoms accompanied by benign prostatic hyperplasia, comprising measuring a slowly-inactivating A-type $K^+$ channel opening activity as an index.

* * * * *